United States Patent
Hoshino (10) Patent No.: US 6,808,264 B1
(45) Date of Patent: Oct. 26, 2004

(54) PUPIL CENTER DETERMINATION RECORDER (75) Inventor: Ryuichi Hoshino, 10-34, Tajima 2-chome, Ikuno-ku, Osaka-shi, Osaka, 544-0011 (JP)

(73) Assignee: Ryuichi Hoshino, Osaka (JP)

( * ) Notice: Subject to any disclaimer, the term of this patent is extended or adjusted under 35 U.S.C. 154(b) by 0 days.

(21) Appl. No.: 10/203,783
(22) PCT Filed: Feb. 14, 2000
(86) PCT No.: PCT/JP01/00804
§ 371 (c)(1),
(2), (4) Date: Aug. 14, 2002
(87) PCT Pub. No.: WO01/58342
PCT Pub. Date: Aug. 16, 2001

(30) Foreign Application Priority Data

Feb. 14, 2000 (JP) ........................................ 2000-034606

(51) Int. Cl.[7] .............................. A61B 3/10; A61B 3/04
(52) U.S. Cl. ....................................... 351/204; 351/231
(58) Field of Search ................................ 351/200, 201, 351/204, 205, 208, 209, 216, 217, 222, 227, 229–231, 246; 33/574, 578

(56) References Cited

U.S. PATENT DOCUMENTS

| 4,160,330 A | * | 7/1979 | Grolman | 33/200 |
|---|---|---|---|---|
| 4,206,549 A | * | 6/1980 | Gould | 33/200 |
| 4,208,800 A | * | 6/1980 | Grolman et al. | 33/200 |
| 4,216,588 A | * | 8/1980 | Richards et al. | 33/574 |
| 4,494,836 A | * | 1/1985 | Cogez | 351/204 |
| 4,653,881 A | * | 3/1987 | Joncour | 351/204 |
| 5,617,155 A | * | 4/1997 | Ducarouge et al. | 351/204 |
| 5,640,775 A | * | 6/1997 | Marshall | 33/28 |
| 5,691,799 A | * | 11/1997 | Ramachandran | 351/204 |

FOREIGN PATENT DOCUMENTS

| JP | 55096920 A | * | 7/1980 | G02C/13/00 |
|---|---|---|---|---|
| JP | 08286158 A | * | 11/1996 | G02C/13/00 |

* cited by examiner

Primary Examiner—Brian L. Casler
Assistant Examiner—John R Sanders
(74) Attorney, Agent, or Firm—Fitch, Even, Tabin & Flannery (57) ABSTRACT A pupil center determination recorder comprising a guide main body 100 attached to a frame of glasses, a pair of adjusters 200 movably attached to the guide main body 100 and pointers 300 respectively attached to the pair of adjusters 200, wherein the pointer 300 has a first marking section 340A for marking the respective objective pupil centers measured by a measurer of the right and left pupils of a test subject on dummy lenses attached to the frame of the glasses worn by the subject, a second marking section 340B for showing identical marks 342B in front of the subject's right and left pupils and a third marking section 340C for marking by moving adjusters 200 such that the identical marks look like overlapping each other and at a position where the identical marks 342B appear to be superimposed; wherein the first, the second, and the third marking sections can move on the same circumference and be fixed at the same position.

3 Claims, 11 Drawing Sheets

PUPIL CENTER DETERMINATION RECORDER

CROSS-REFERENCED APPLICATIONS

This application is a National phase of International Application PCT/JP01/00804, filed 5 Feb. 2001 which designated the U.S. and that International Application was published not under PCT Article 21(2) in English.

BACKGROUND OF THE INVENTION

The invention relates to a pupil center determination recorder to make agree the optical center of a lens with the pupil center of a spectacled user in making the glasses.

DISCLOSURE OF THE PRIOR ART

The major components of glasses are a frame and lenses. A frame is mainly selected in view of its fashionability, while lenses are selected in accordance with user's eyesight. The most important thing in making glasses is to make the optical center of each lens agree with user's pupil center. The deviation of the optical center from the pupil center exhibits no performance even if the lenses meet the eyesight, resulting in shoulder stiffness or systemic fatigue, in the worst case, pathologic conditions including heterotopias.

The biggest factor of the deviation of the optical center from the pupil center in glasses is that the optical center of each lens is adjusted to an average position of the pupil center in spite of the fact that each user has a different face shape, namely the position of the pupil center varies according to users.

As stated in Japanese Unexamined Patent Publication No. 8-47481 (No. 47481/96), a device to make the optical center agree with the pupil center has been already proposed. It is designed to decide the center of the pupils in a frame by inputting the image of a user wearing the frame for deciding the coordinate of the pupil center.

In this method, however, the measurer determines the coordinates of the pupil center as the pupil center of the user (subject). Accordingly, in many cases, the position deviates from the position considered to be the true pupil center by the subject.

The true pupil center regarded by the subject means the pupil centers of the both eyes when the subject looks at a distant view 2–3 meters away from him and the same marks shown in front of both eyes are overlapped each other. Thus, the position regarded as the pupil center by the measurer is named an objective pupil center, while the position regarded as the pupil center by the subject is named a subjective pupil center. Explanation of them are made in the following:

Since about 5–6 mm deviation often exists between the objective pupil center and the subjective pupil center, it is not possible to make glasses on the basis of the subjective pupil center by the method stated in above mentioned official gazette.

SUMMARY OF THE INVENTION

This invention has been originated from the viewpoint of the above circumstances.

An object of the invention is to provide a pupil center determination recorder, which verifies the pupil center by consideration of the objective pupil center and the subjective pupil center to make the pupil center agree with the optical center of lenses.

A pupil center determination recorder of the present invention can accomplish the above object.

The recorder comprises a guide main body to be attached to a frame of glasses worn by a subject, a pair of adjusters movably attached to the guide main body, and pointers respectively attached to the pair of adjusters, wherein the pointer has a first marking section for marking the right pupil center and the left pupils center of the subject measured by a measurer on dummy lenses attached to the frame of the glasses worn by the subject, a second marking section for displaying identical marks in front of the subject's right and left pupils and a third marking section for moving the adjusters so as to superimpose the identical marks at least partially over each other and for marking the right pupil center and the left pupil center on the dummy lenses at a position where the marks appear to be superimposed. The first, second, and third marking sections can move on the same circumference and be fixed at the same position.

According to the invention, it is desirable that the center of the mark shown by the second marking section is transparent one with ring shape.

The marking by the third marking section is carried out by sticking a seal with the same mark as that shown by the second marking section to each dummy lens.

The invention is designed as described above and therefore exerts the following effects.

The third marking section marks the subjective pupil center on each dummy lens simply by verifying the objective pupil center in the first marking section, and by verifying the subjective pupil center in the second marking section. The result determines the pupil center after considering the objective pupil center and the subjective pupil center. The use of the recorder prevents problems, including shoulder stiffness, systemic fatigue, caused by disagreement between the optical center and the pupil center observed in conventional lenses. Easy adjustment of glasses having disagreement between the optical center and the pupil center is possible, which contributes to elimination of the above problems.

The center part of the mark exhibited by the second marking section is of a transparent ring-shape, accordingly easy verification for the subjective pupil center is allowed.

The marking done by the third marking section readily allows repeated marking by sticking the seal having the same mark as that exhibited by the second marking section to each dummy lens, verifying the pupil center more exactly.

Other objects, features, aspects and advantages of the invention will become more apparent from the following detailed description of embodiments with reference to the accompanying drawings.

DETAILED DESCRIPTION OF THE EMBODIMENTS

Figure 1:
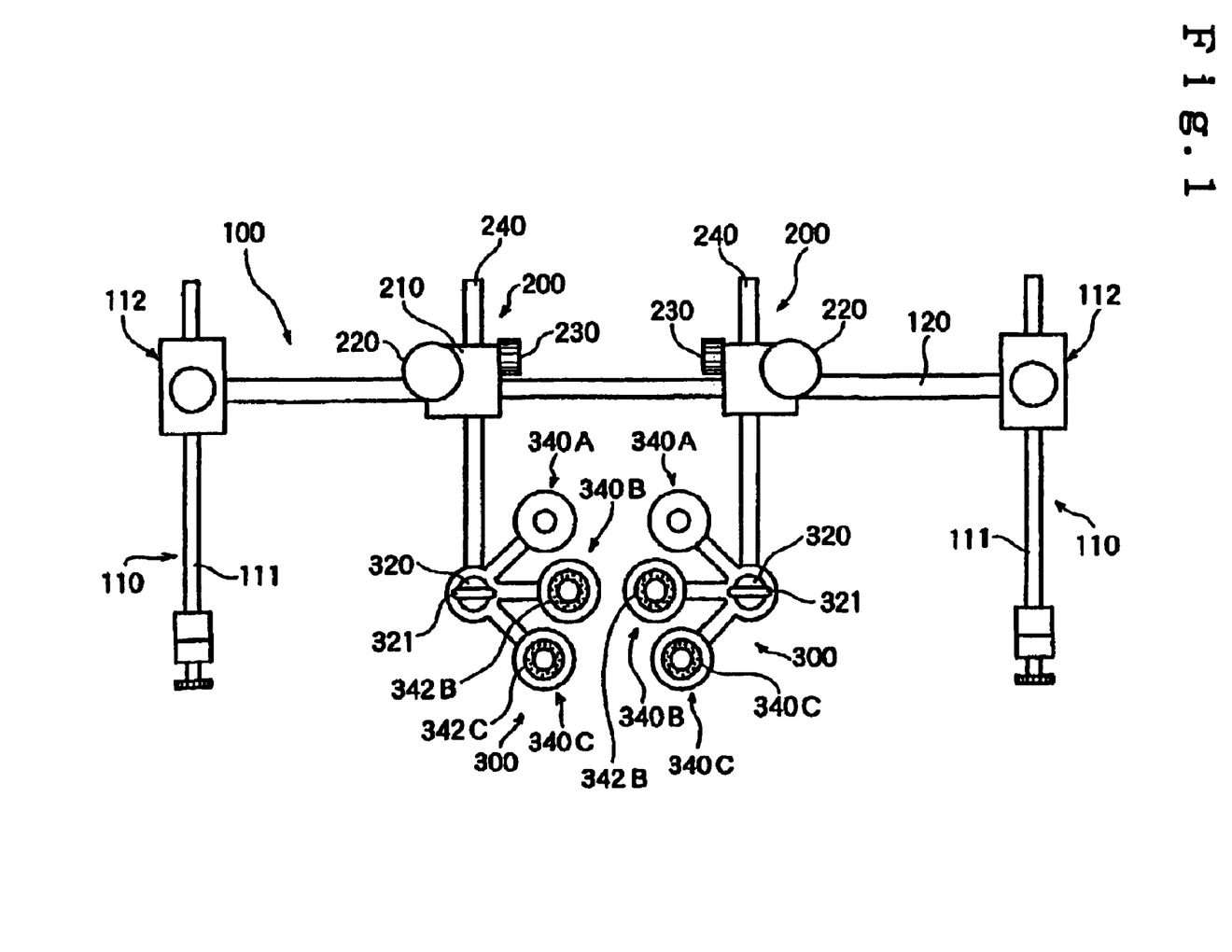
FIG. 1 is a schematic front view of a recorder for verifying the pupil center embodying the present invention.
Figure 2:
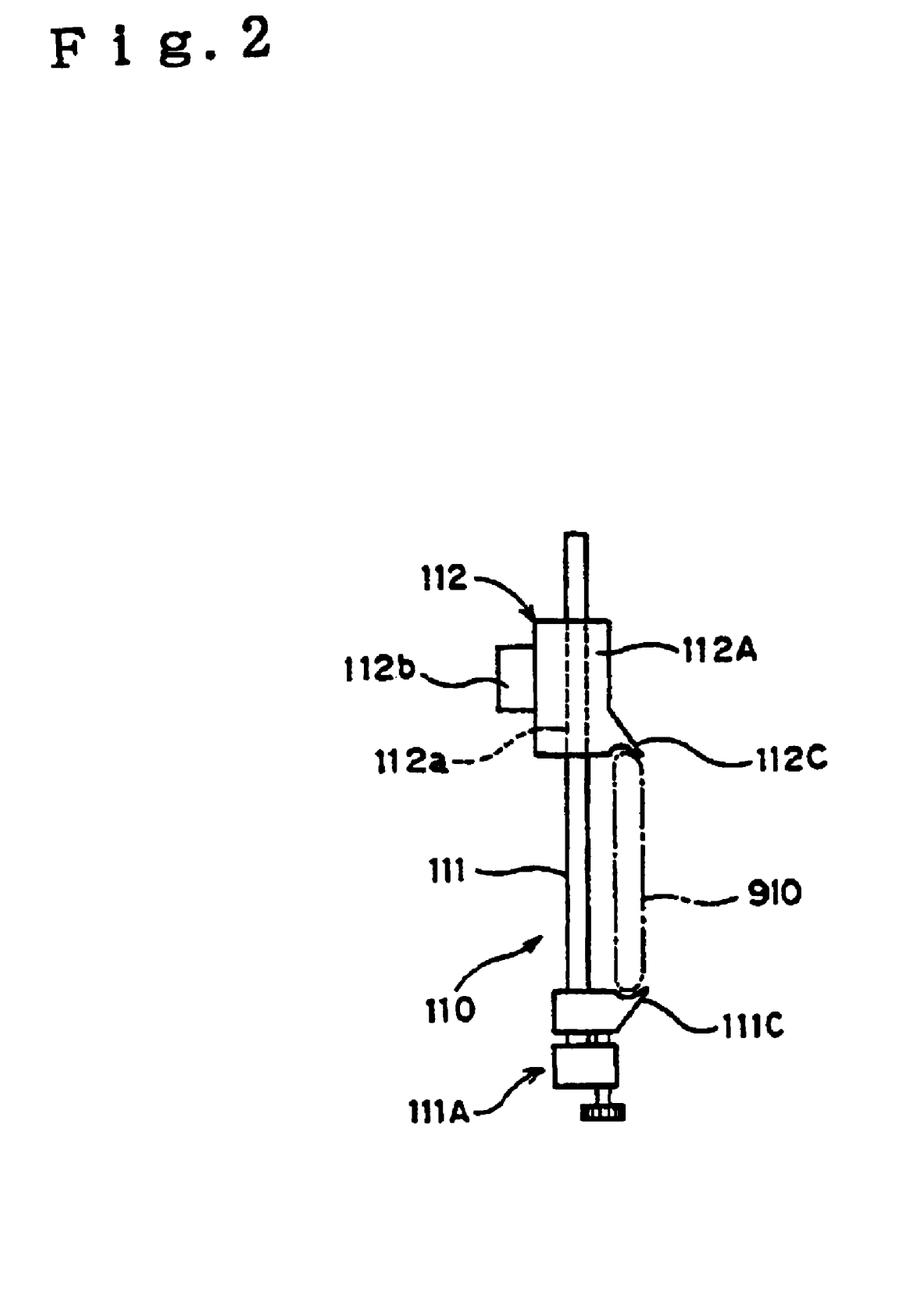
FIG. 2 is a schematic side view illustrating the clamp section of the recorder embodying the present invention.
Figure 3:
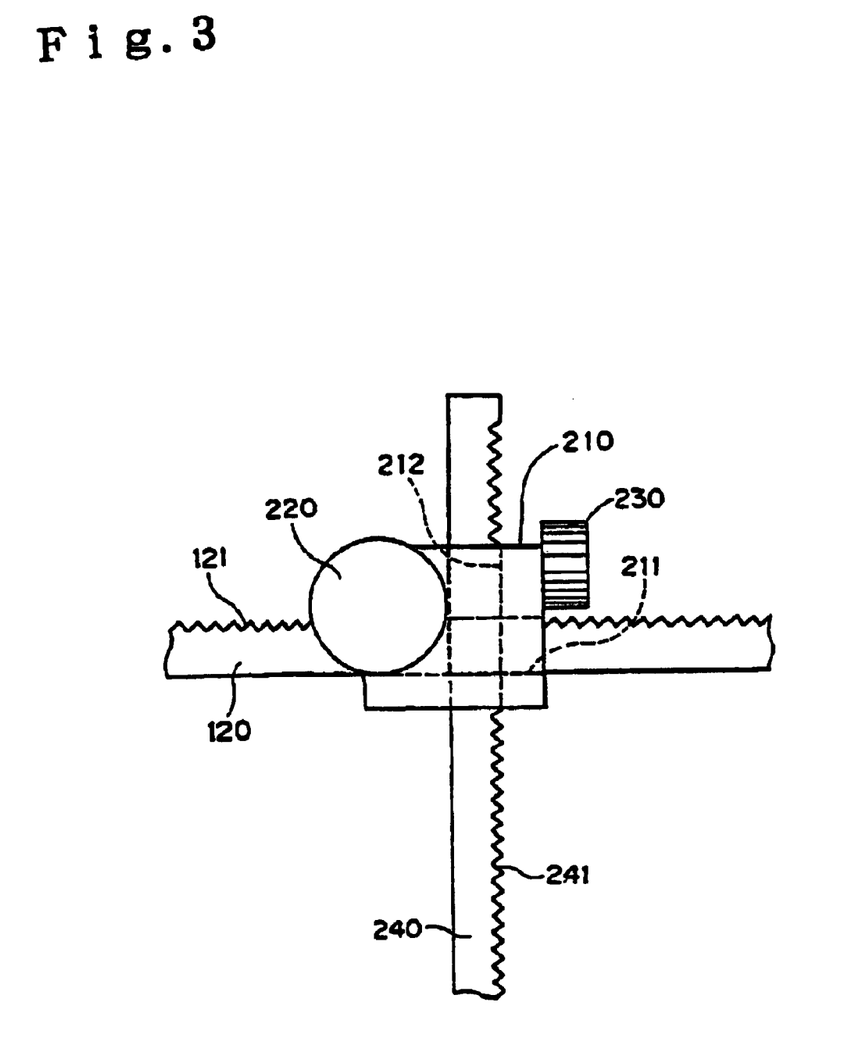
FIG. 3 is a schematic front view illustrating the major section of the adjuster of the recorder embodying the present invention.
Figure 4:
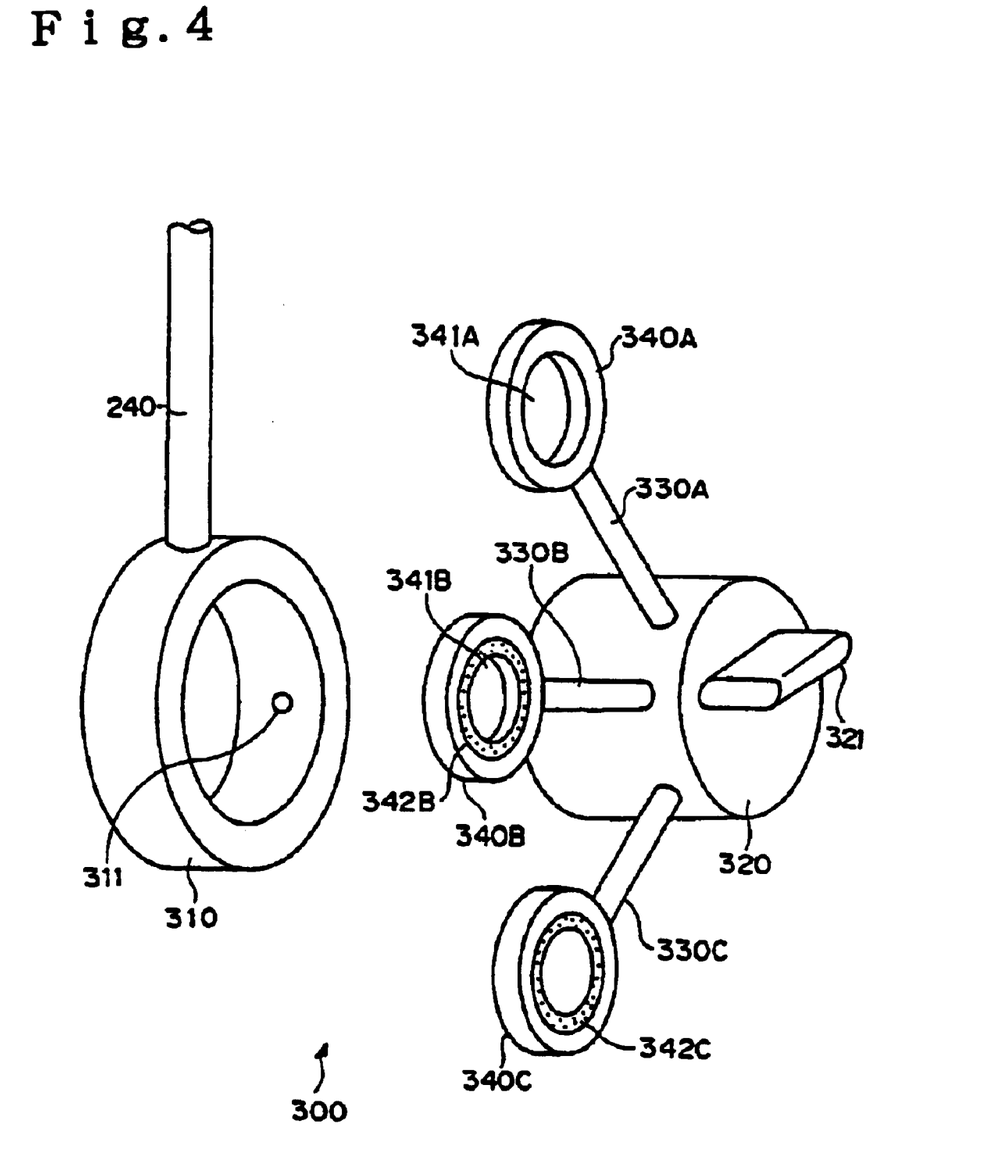
FIG. 4 is a schematic exploded perspective view of the pointer of the recorder embodying the present invention.
Figure 5:
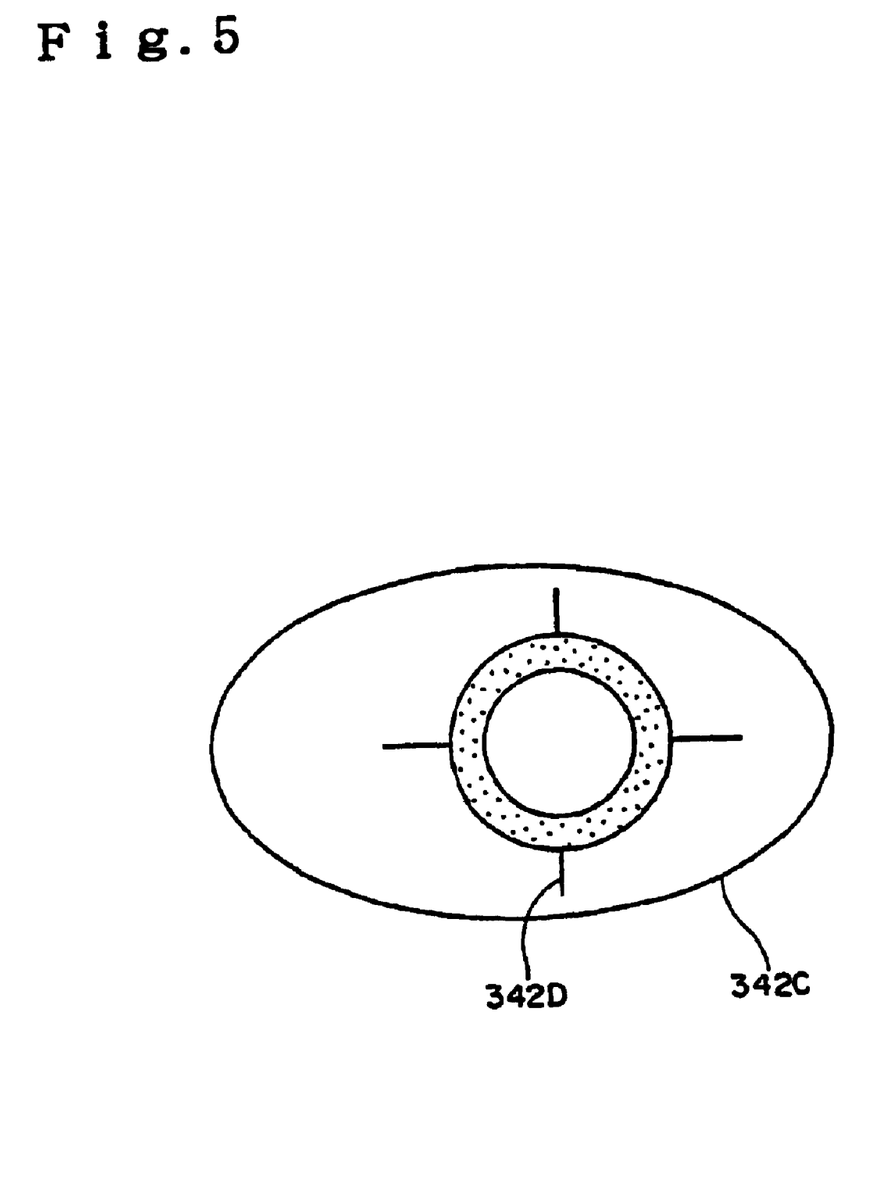
FIG. 5 is a schematic plan view of the seal used for the recorder embodying the present invention.

FIG.1 illustrates a schematic front view of a recorder for verifying the pupil center relating to the mode for carrying out the invention, FIG.2 shows a schematic side new illustrating the clamp section of the recorder embodying the present invention, FIG. 3 indicates a schematic front view illustrating the major section of the adjuster of the recorder embodying the present invention, FIG.4 illustrates a schematic exploded perspective view of the pointer of the reorder embodying the present invention, and FIG.5 shows a schematic plan view of the seal used for the recorder embodying the present invention.

Figure 6:
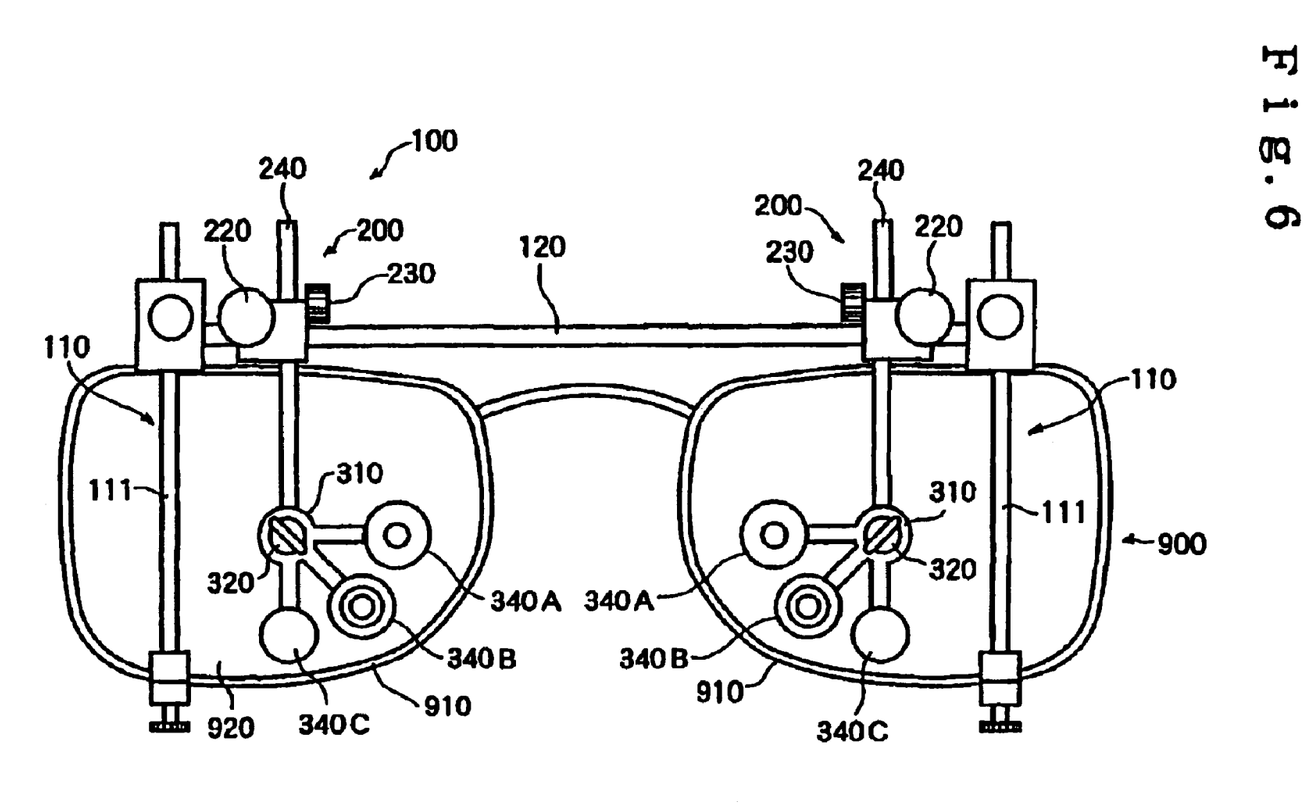
FIG. 6 is a schematic front view of verification work for the pupil center by the use of the recorder embodying the present invention.
Figure 7:
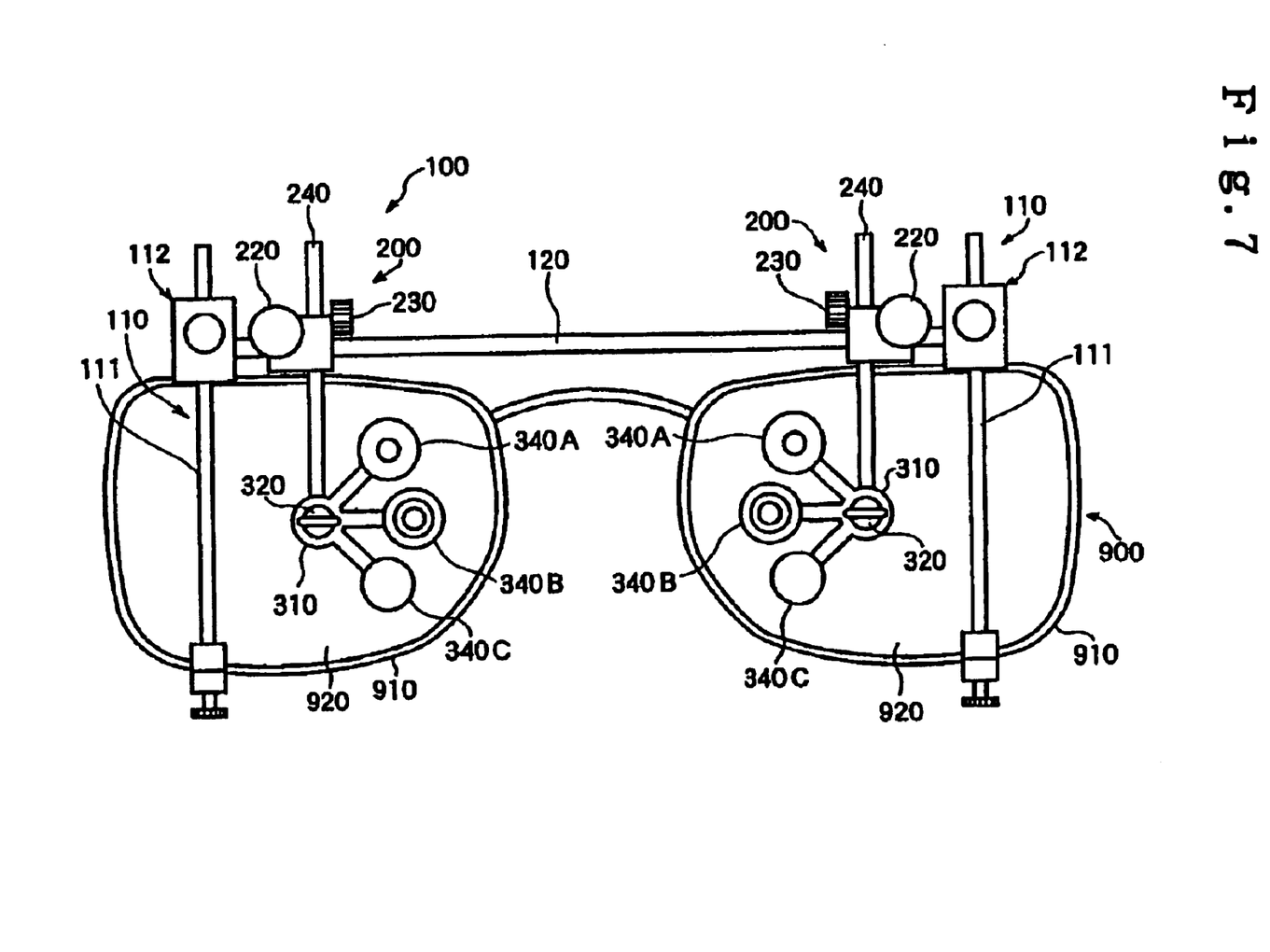
FIG. 7 is a schematic front view of verification work for pupil center by the use of the recorder embodying the present invention.
Figure 8:
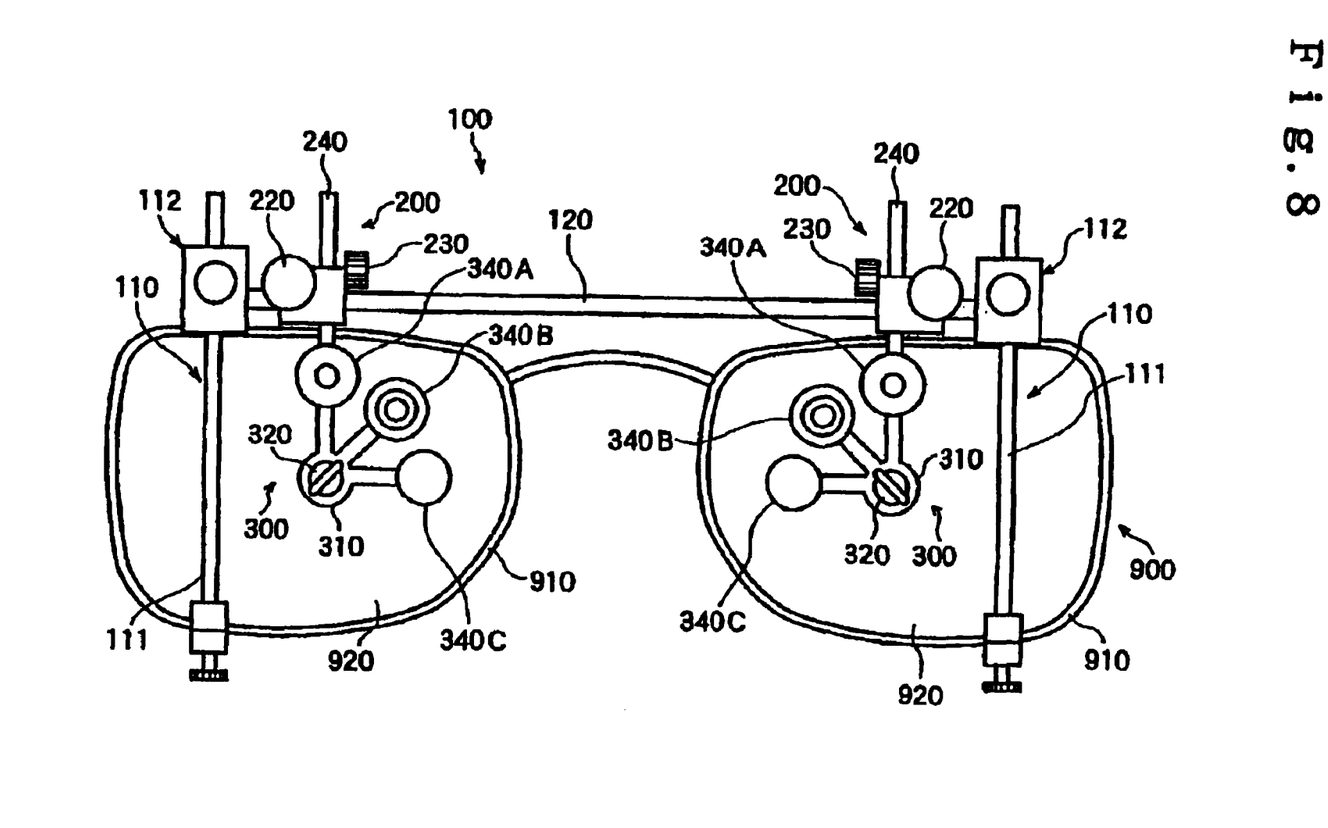
FIG. 8 is a schematic front of view of verification work for pupil center by the use of the recorder embodying the present invention.
Figure 9:
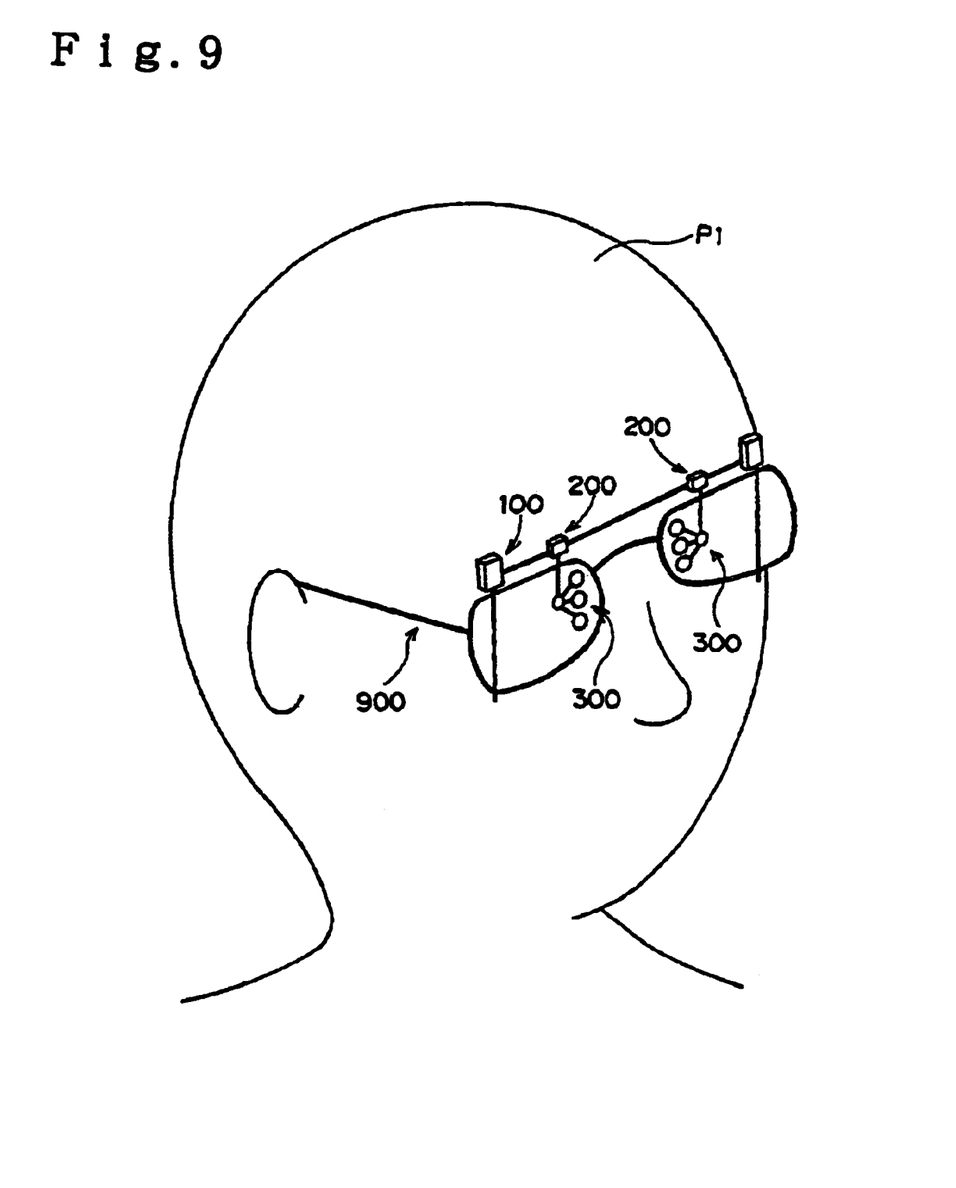
FIG. 9 is a schematic perspective view of verification work for the pupil center by the use of the recorder embodying the present invention.
Figure 10:
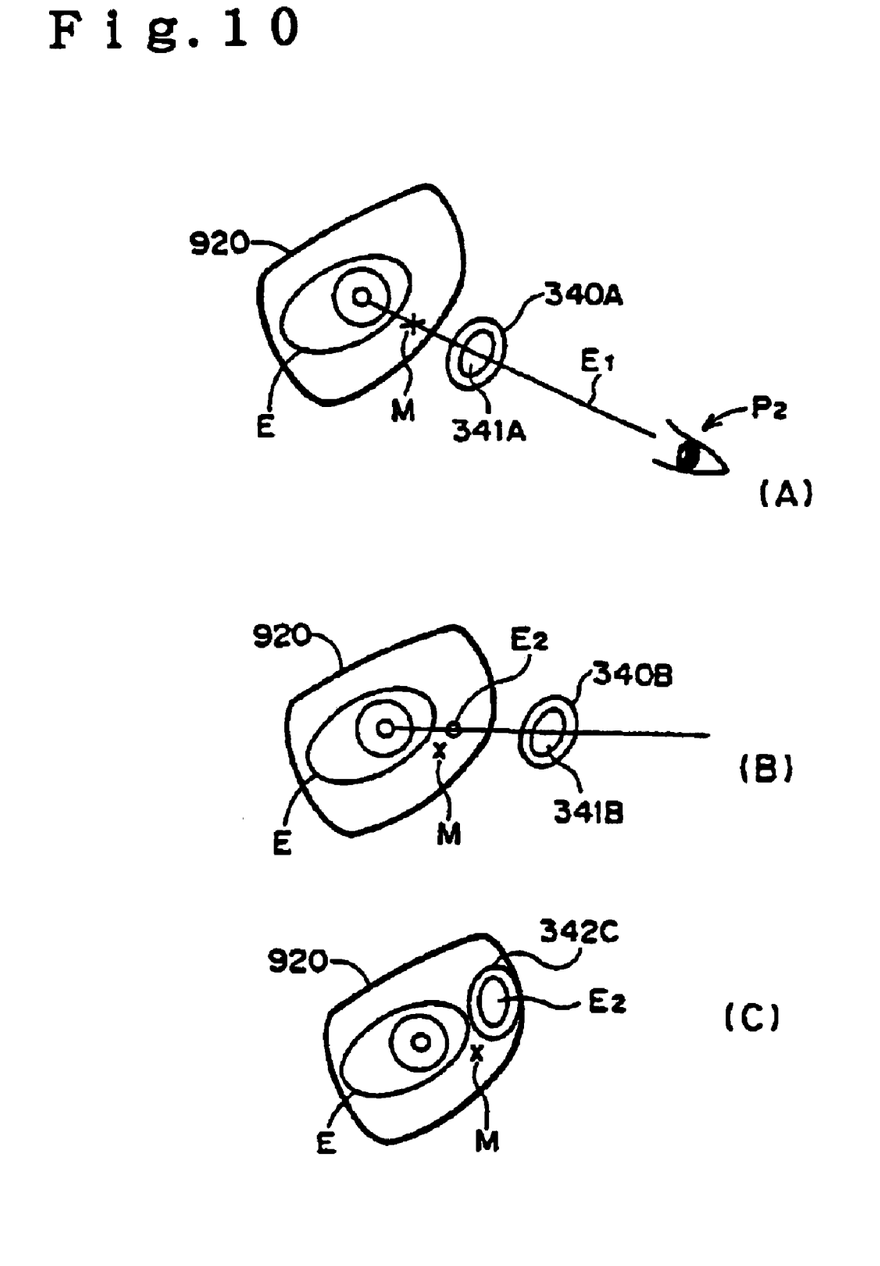
FIG. 10 is a schematic illustrational view of the principle of the verification work for the pupil center by the use of the recorder embodying the present invention.
Figure 11:
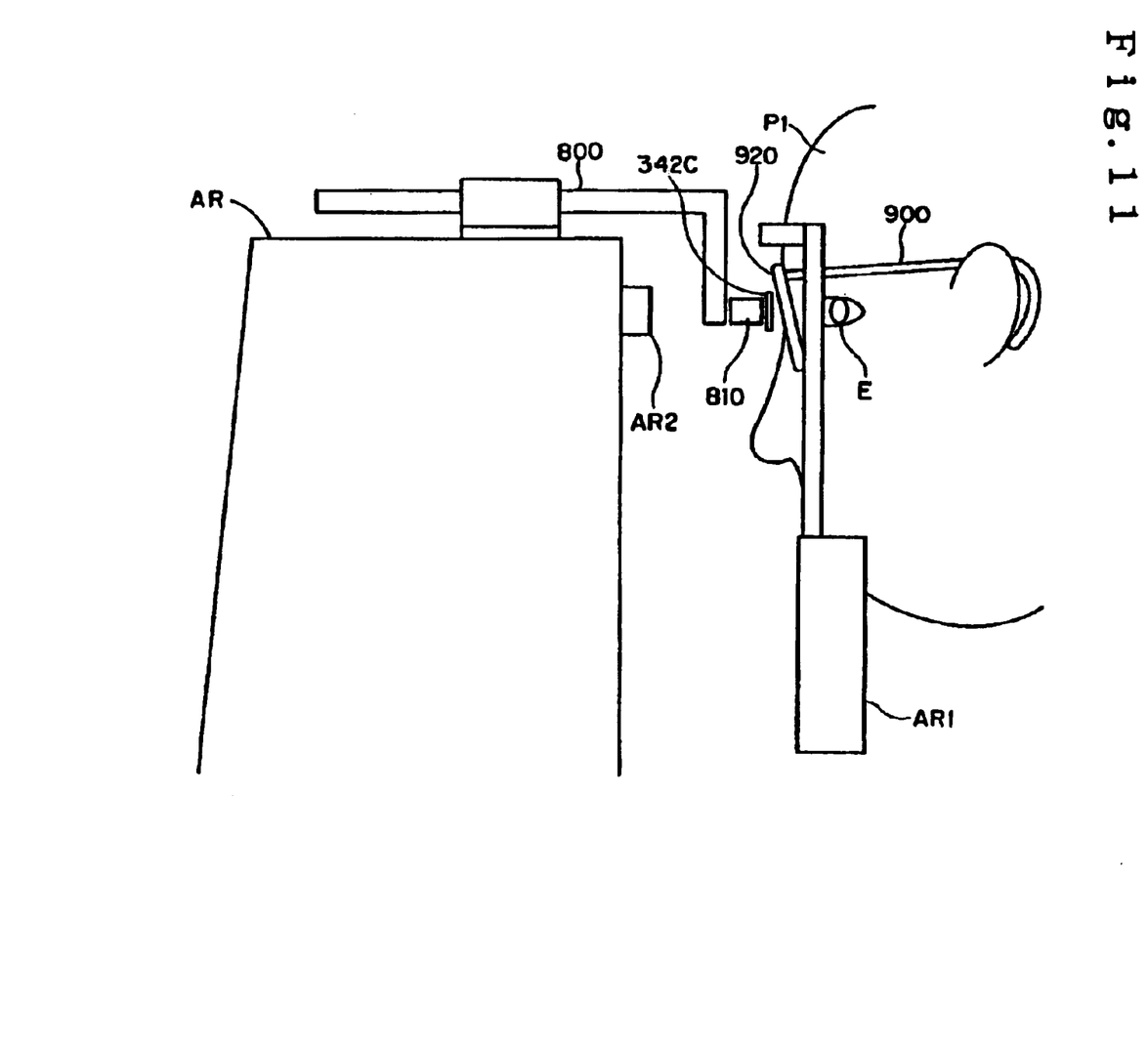
FIG. 11 is a schematic illustrational view applying an automatic refract meter to the recorder embodying the present invention.

The schematic front view indicating the verification work of the pupil center by using the recorder embodying the present invention is shown in FIGS. 6, 7 and 8, respectively. A schematic perspective view indicating the verification work of the pupil center by using the recorder embodying the present invention is shown in FIG. 9. A schematic explanation view indicating the principle of the verification work of the pupil center by using the recorder embodying the present invention is shown in FIG.10. A schematic explanation view of applying the recorder of the present invention to an auto refract meter is shown in FIG. 11.

The recorder for verifying the pupil center embodying the present invention comprises a guide main body 100 attached to the frame 900 of glasses worn by a subject P1 to be inspected, a pair of adjusters 200 movably attached to the guide main body 100, and pointers 300 attached to the pair of adjusters 200. The pointer 300 has a first marking section 340A for marking the respective pupil centers (the objective pupil center El) of right and left pupils E of the subject P1 observed by an observer P2 on dummy lenses 920 attached to the frame 900 of the subject's glasses, a second marking section 340B showing the same mark 342B in front of the right and left pupils E of the subject P1, and a third marking section 340C for moving the adjuster 200 to superimpose at least partially the same marks 342B and for carrying out marking exhibiting the respective pupil centers (subjective pupil center E2) of the right and left pupils E on the associated dummy lenses 920. The first,second and third marking section 340A, 340B, 340C, respectively, move on the same circumference to fix at the same position.

The guide main body 100 has a pair of clamp sections 110 to be attached to the frame 900 of the glasses. Each clamp section 110 is designed to vertically hold a rim 910 of a frame 900.

Each clamp section 110 has a clamp side shaft 111 having a stationary part 111A at its lower end and a clamp side shaft fixing section 112 for fixing the clamp section 110 to the rim 910 with the clamp side shaft 111 penetrating through the clamp side shaft fixing section 112. Each camp side shaft fixing section 112 has a blocked clamp side mobile part 112A having a through hole 112a into which the clamp side shaft 111 penetrates and a screw section 112b screwed in the clamp side mobile part 112A with its tip end reaching the through hole 112a. The clamp side mobile part 112A is provided at its lower end with a downward upper side claw section 112c The stationary part 111A has an upward lower side clamp claw section 111c at its upper end. The stationary part 111A is provided with a screw part 111b for moving the lower side claw section 111c.

The frame rim 910 and also the frame 900 are fixed to each lens by grasping the rim 910 with both claw section 111c and 112c, by moving the clamp side mobile part 112A along the clamp side shaft 111, and then by fixing the clamp side shaft 111 through the use of the screw section 112b.

A pair of right and left clamp sections 110 are connected to each other through a main shaft 120. A rack 121 is formed on the top surface of the main shaft 120. (See FIG.3). The rack 121 is used for moving the adjusters 200 in the right and the left directions.

In this way the guide main body 100 is roughly composed of a pair of clamp sections 110 and the main shaft 120 for connecting the pair of clamp sections 110 to each other like a gate shape.

As shown in FIG.3, each adjuster 200 has a blocked adjuster side mobile part 210 having a horizontally penetrated horizontal though hole 211 and a vertically penetrated vertical through hole 212, a horizontal pinion section 220 rotationally movably attached to the adjuster side mobile part 210 with its tooth section being exposed to the horizontal through hole 211, a vertical pinion section 230 with its tooth section being exposed to the vertical through hole 212 and an adjuster side shaft 240 inserted in the vertical through hole 212.

The man shaft 120 is penetrated through horizontal through hole 211 of the adjuster side mobile part 210 to engage the tooth section of the horizontal pinion section 220 with the rack 121 of the main shaft 120. It the horizontal pinion section 220 is turned, the adjuster side mobile part 210 moves in the transverse direction along the main shaft 120.

A rack 241 is formed on the adjuster side shaft 240. The rack 241 is engaged with the tooth section of the vertical pinion section 230. If the vertical pinion section 230 is turned, the adjuster side shaft 240 moves in the vertical direction.

Each pointer 300 has a generally ring-shaped frame section 310 provided on a tip end of the adjuster side shaft 240, a hub section 320 rotationally movably engaged with the interior of the frame section 310, outwardly projecting three arms 330A, 330B, 330C provided on the hub section 320 and outwardly projected with the hub section 320 being engaged with the frame section 310, and a first marking section 340A, a second marking section 340B and a third marking section 340C provided on tip ends of the arm sections 330A, 330B, 333C, respectively.

An interior of the frame section 310 has small balls 311 inwardly elastically biased by internal springs respectively. Three recesses (not shown in a drawing) are formed at 45 degree-intervals in the outer periphery of each arm section 330A-, 330B-, 330C-free side of the hub section 320. Engaging the small balls 311 with recesses, respectively anchors the rotationally moving position of the hub section 320 in the frame section 310.

The hub section 320 has portions protruded from the frame section 310 even if the hub section 320 is engaged with the frame section 310. The three arm sections 330A, 330B, 330C are protruded and formed at 45 degree-intervals at the portions. The three arm sections 330A, 330B, 330C are equal in length. The hub section 320 is provided with a knob 321 held with a hand in rotationally moving the hub section 320.

The uppermost arm section 330A is provided at its tip end with the first marking section 340. The first marking section 340A is of a ring shape having an opening 341A, of such a size that an measurer P2 may verify the pupil center (objective pupil center E1) of each pupil E of the subject P1.

The central arm section 330B is provided at its tip end with the section marking section 340B. The second marking section 340B is of a generally ring shape and has an opening 341B with the same size as that of the first marking section 340A. The opening 341B is provided with a mark 342B having a transparent center and an orange ring-like periphery.

The lowermost arm section 330C is provided at its tip end with the third marking section 340C. As shown in FIG.5, the third marking section 340C has a seal 342C having the same pattern, namely a transparent center and an orange periphery, as those of the mark 342B. The seal 342C has a printed crisscross reticule 342D serving as a guide to verify the subjective pupil center E2.

As mentioned above, the three arm sections, 330A, 330B, 330C are equal in length and are formed at 45-degree intervals like the three recesses in the frame section 310. Thus, if the hub section 320 is turned, they move on the same circumference and they can be fixed at the same position.

Now, explanation is made to work for verifying the pupil center by the use of the recorder having the above configuration.

Firstly, the frame 900 of the glasses selected by the subject P1 is attached to the guide main body 100 of the recorder. Namely, the frame 900 is clamped by the use of the clamp section 110. Upwardly and downwardly holding the rim 910 of the frame 900 with the aid of the upper side claw section 112c and the lower side claw section 111c of the clamp section 110 fixes the frame 900 to the guide main body 100. Each dummy lens 920 is previously attached to the rims 910 of the frame 900.

Secondary, as shown FIG.9, the subject P1 wears the frame 900 on which the recorder is fixed through the guide main body 100. It is important to wear the frame 900 at the same position as that used for ordinary spectacle application.

As shown in FIG.6, the hub section 320 of the pointer 300 is turned to direct the arm section 330A having the first marking section 340A horizontally. As shown in FIG. 10(A), if the adjuster 200 is adjusted vertically and laterally to bring the first marking section 340A observed from the measurer P2 side into agreement with the pupil center E1 (objective pupil center) of each pupil E. Marking M in white ink is applied to each dummy lens 910 through the opening 341A of the first marking section 340A. The marking M is applied to the right and the left pupils.

Finally as shown in FIG. 7, the hub section 320 of the pointer 300 is turned to horizontally set the arm section 330B having the second marking section 340B. The first marking section 340A and the second marking section 340B are designed to move on the same circumference, and these sections are fixed at the same position. This makes the position of the opening 341B of the second marking section 340A agree with the position of the opening 341A of the first marking section 340A. Consequently, the opening 341B of the second marking section 340B agrees with the marking in white ink.

The subject P1 looks at a distant view, 2–3 meters or longer in this state. If the objective pupil center E1 coincides with the subjective pupil center E2, the marks 342B provided on the pair of second marking sections 340B, respectively, should be superposed. If the marks 342B are not superimposed on each other, the two adjusters 200 are horizontally or vertically moved such that they are superimposed on (over) each other. The position where the marks 342B are superimposed over the subjective pupil center E2. (See FIG. 19 (B)).

The adjuster section 200 is fixed at the position where marks 342 are superposed. In this state, the second marking section 340B is replaced with the third marking section 340C. (See FIG. 8). As shown in FIG. 10(C), seals 342C provided on the third marking section 340C are stuck to the right and the left dummy lenses 920 respectively. The seal 342C-stuck position is the subjective pupil center E2.

Coordinates (the coordinates of the subjective pupil center E2) at the rim 910 of the frame 900 at the transparent center of the seal 342C stuck to each dummy lens 920 are measured. The coordinates can be measured using conventional charts. The resulting coordinate data is fed to lens-finishing equipment. The lens is finished such that the optical center of the finished lens agrees with the coordinates. The optical center of the lens surely agrees with the subjective pupil center E2 of the subject P1.

Although the present invention is applied to the frame of the lens in this embodiment, the invention can also be applied to a contact lens and to measurement for a squint.

A bifocal lens has and optical center for a distant view and an optical center for a near view. The use of the recorder permits easy agreement of both optical centers and the respective pupil centers.

Explanation is made on the application of the recorder to an automatic refract meter AR.

The automatic refract meter AR automatically detects the refractive index and the objective pupil center of each pupil E of the subject P1 by irradiating each pupil E of the subject P1 with an infrared beam and then by detecting its reflection. The automatic refract meter AR has a stand AR1 on which the jaw of the subject P1 is placed, a moving mechanism (not shown in a drawing) for horizontally and vertically moving the stand AR1 in four directions, an irradiation section (not shown in a drawing) for irradiating each pupil E of the subject P1 with the infrared beam, an arithmetic section (not shown in a drawing) for computing the refractive index of each pupil E with the aid of the infrared beam reflected from each pupil E, an image pick-up section AR2 for picking up the image of the pupil E of the subject P1, with the jaw of the subject P1 placed on the stand AR1 and a display section (not shown in a drawing), including a CRT for displaying each pupil E imaged by means of the image pick-up section AR2.

The recorder is installed on the automatic refract meter AR. As shown in FIG.11, the seal 342C has been designed to be stuck to each dummy lens 920 attached to the fame 990 of the user's glasses. The casing of the automatic refract meter AR at its upper part has a rod section 800 capable of advancing/retreating to/from each dummy lens 920, a seal sticking section 810 provided at the tip end of the arm section 800, and a seal 342C attached to the seal sticking section 810.

When the objective pupil center E1 is verified by means of the automatic refract meter AR, the stand AR1 is then fixed to the jaw of the subject P1. The rod section 800 is pressed against the subject P1. Finally, the seal 342C attached to the seal sticking section 810 is stuck to a dummy lens 920. The above are applied to the right and the left pupils E.

In this state, the jaw of the subject P1 is removed from the stand AR1. Verification is made to assure that the seals 342C stuck to the right and the left dummy lenses 920 are superposed. When the result is positive, each objective pupil center E1 agrees with each subjective pupil center E2. The measurement for measuring the coordinate (the coordinate of the subjective pupil center E2) in the rim 910 of the frame 900 at the center thereof in the transparent seal 342C area is available by the user of a conventional chart. The resulting coordinate data is fed to the lens-finishing equipment to finish each lens in such a manner that the optical center of the finished lens may agree with the coordinate.

The negative result means disagreement between the objective pupil center E1 and the subjective pupil center E2. Where, the adjuster 200 is moved in the right and the left direction to make the subjective pupil center E2 agree with the objective pupil center El. The work after verifying the agreement of the subjective pupil center E2 is the same as the work mentioned above.

The application of the recorder to the automatic refract meter AR enables exact and prompt agreement of the objective pupil center E1 and the subjective pupil center E2. The same is true for the verification of the subjective pupil center E2.

What is claimed is:

1. A pupil center determination recorder comprising: a guide main body to be attached to a frame of glasses worn by a subject, a pair of adjusters movably attached to the guide main body and pointers respectively attached to the pair of adjusters, wherein the pointer has a first marking section for marking the right pupil center and the left pupil center of the subject measured by a measurer on dummy lenses attached to the frame of the glasses worn by the subject; a second marking section for showing identical marks in front of the subject's right and left pupils; and a third marking section for moving the adjusters so as to superimpose the identical marks sufficiently over each other and for marking the right pupil center and the left pupil center on the dummy lenses at a position where the marks appear to be superimposed; wherein the first, second, and third marking sections can move on the same circumference and be fixed at the same position.

2. A pupil center determination recorder according to claim 1, wherein the center of the mark shown by the second marking section is transparent and has a ring shape.

3. A pupil center determination recorder according to claim 2, wherein the marking by the third marking section is carried out by sticking a seal having the same mark as that shown by the second marking section to respective dummy lenses.

* * * * *